United States Patent
Stierstorfer

(10) Patent No.: US 7,623,618 B2
(45) Date of Patent: Nov. 24, 2009

(54) METHOD FOR SCATTERED RADIATION CORRECTION IN X-RAY IMAGING, AND X-RAY IMAGING SYSTEM FOR THIS PURPOSE

(75) Inventor: Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 8 days.

(21) Appl. No.: 11/896,213

(22) Filed: Aug. 30, 2007

(65) Prior Publication Data

US 2008/0232546 A1    Sep. 25, 2008

(30) Foreign Application Priority Data

Aug. 31, 2006 (DE) .................. 10 2006 040 852

(51) Int. Cl.
*A61B 6/00* (2006.01)
(52) U.S. Cl. .......................................... 378/7; 378/98.4
(58) Field of Classification Search ................ 378/7, 378/22–27, 62, 70, 87, 98.4
See application file for complete search history.

(56) References Cited

U.S. PATENT DOCUMENTS 5,666,391 A    9/1997    Ohnesorge et al.
7,190,758 B2    3/2007    Hagiwara
2007/0104310 A1    5/2007    Nottling et al.

FOREIGN PATENT DOCUMENTS

| DE | 10 2005 053 498 A1 | 11/2005 |
|---|---|---|
| EP | 0 660 599 B2 | 8/2002 |
| EP | 1 502 548 A1 | 2/2005 |

*Primary Examiner*—Edward J Glick
*Assistant Examiner*—Mona M Sanei
(74) *Attorney, Agent, or Firm*—Harness, Dickey & Pierce, P.L.C.

(57) ABSTRACT

The present invention relates to a method for scattered radiation correction in X-ray imaging, and to an X-ray imaging system for carrying out the method. In the method, measurement signals t from an X-ray detector (9) are digitized and converted to logarithmic form, with these measurement signals t having been obtained by radiation through an examination object (10) by the X-ray detector (9). Correction values which have been obtained from a series development of a logarithm $\ln(1-s/t)$ are subtracted from the measurement signals that have been converted to logarithmic form, with this series development being terminated at the earliest after the first order, where s denotes a previously determined scattered radiation signal from radiation passed through the examination object (10). The method and the associated X-ray imaging system allow scattered radiation to be corrected for with increased accuracy, on the basis of measurement signals that had been converted to logarithmic form.

15 Claims, 3 Drawing Sheets

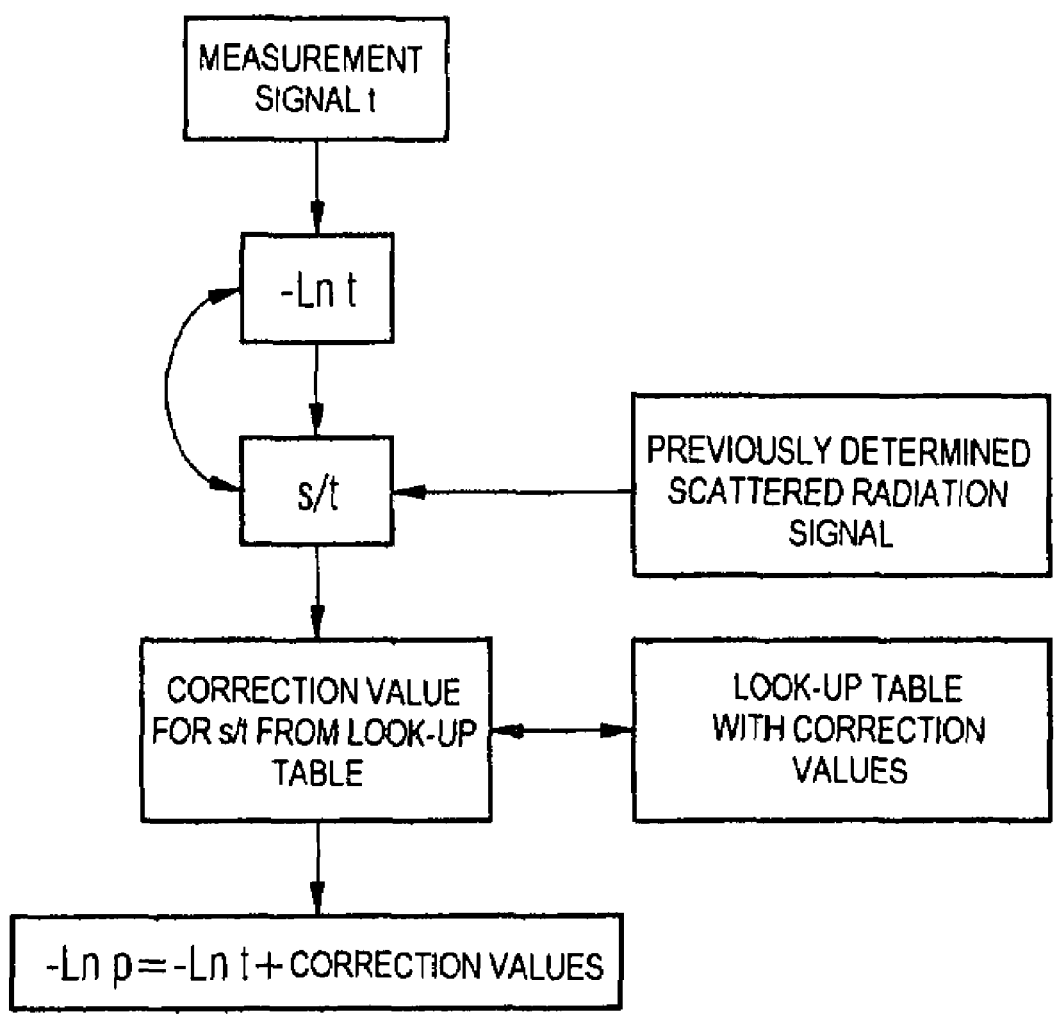

METHOD FOR SCATTERED RADIATION CORRECTION IN X-RAY IMAGING, AND X-RAY IMAGING SYSTEM FOR THIS PURPOSE

The present invention relates to a method for scattered radiation correction in X-ray imaging, in which measurement signals from an X-ray detector are digitized and converted to logarithmic form, with the measurement signals being obtained from the X-ray detector when radiation is passed through an examination object. The invention also relates to an X-ray imaging system which is designed to carry out the method.

For X-ray imaging purposes, X-ray radiation is passed through an examination object in at least one direction, and the intensity of the X-ray radiation striking an X-ray detector opposite the X-ray source is measured on a position-resolved basis. The measured intensity I is dependent on the absorption characteristic of the material through which the radiation is passed, and on the distance that the X-ray beam travels over when passing through the object. The measured intensity I is in this case exponentially dependent on the input intensity $I_0$, in accordance with the absorption law, in which case: $I/I_0 = e^{-s\mu(x)dx}$. For X-ray imaging purposes, the signal processing is generally carried out by digitizing the measured signals and converting them to logarithmic form, thus making it possible to obtain the attenuation value distribution $\mu(y, z)$ or $\mu(x, y, z)$ of the examination object. Signals that have been converted to logarithmic form are also used for processing in computer tomography (CT).

Scattered radiation represents a fundamental problem in X-ray imaging and leads to a reduction in the image contrast, in particular to undesirable brightness smearing over the entire image. Scattered radiation occurs because the primary radiation that propagates on a straight line between the X-ray source and the respective detector element is scattered on individual volume elements of the examination object, and the second radiation resulting from this then also strikes other detector elements in the X-ray detector, where it increases the measured signal intensity. Despite the use of so-called scattered beam grids upstream of the X-ray detector, it is impossible to avoid a scattered beam component in the measured signal. The scattered beam signal which strikes the X-ray detectors is therefore frequently subtracted by calculation from the measured signal in order to obtain the intensity of the primary radiation. The respective scattered beam signal is in this case either estimated by computation or is determined, at least approximately, on the basis of previously carried out measurements, in particular using a measurement phantom. In this case, each detector element in the X-ray detector, for example a two-dimensional X-ray detector array or a detector arrangement with one or two rows, can also produce a different scattered beam signal, so that the scattered radiation correction is then carried out with a possibly different value of the scattered beam signal for each detector element.

Until now, the scattered beam signal has been subtracted from the measured and digitized detector signal before conversion of the measurement signals to logarithmic form. However, this subtraction process can result in very small or even negative values which lead to problems during the subsequent logarithmic conversion process, and also greatly increase the noise. In order to avoid this problem, it is therefore proposed that the scattered radiation be corrected by multiplication. The corrected signal, the primary radiation p, is then obtained from the measured signal t and the estimated scattered radiation s using:

$$p = t\frac{t}{t+s}.$$

This correction by multiplication is obtained from an approximation, in which the correction by subtraction is approximated by a series development:

$$P = t - s = t\left(1 - \frac{s}{t}\right) = t\frac{1}{1 + \frac{s}{t} + \left(\frac{s}{t}\right)^2 + \left(\frac{s}{t}\right)^3 + \left(\frac{s}{t}\right)^4 + \ldots},$$

by terminating this sum formula for the geometric series after the first order.

The object of the present invention is to specify a method for scattered radiation correction in X-ray imaging, and an X-ray imaging system for this purpose, which avoid the problems of negative values and of increased noise, and lead to greater accuracy in the scattered radiation correction.

The object is achieved by the method and the X-ray imaging system as claimed in patent claims 1 and 6. Advantageous refinements of the method and of the X-ray imaging system are the subject matter of the dependent claims, and can be found in the following description and in the exemplary embodiment.

In the present method for scattered radiation correction for X-ray imaging, the measurement signals t which are obtained from the X-ray detector when radiation is passed through an examination object are digitized and converted to logarithmic form. Correction values which have been obtained from a series development of the logarithm ln(1–s/t) are then subtracted from the measurement signals lnt that have been converted to logarithmic form, with this series development being terminated at the earliest after the first order. In this case, s is a previously determined scattered beam signal from radiation being passed through the examination object.

In the present method, the scattered radiation correction is therefore carried out only after the measurement signals have been converted to logarithmic form, with a series development of the logarithm being used for correction. In this case, the values that have been converted to logarithmic form are corrected using the following formula:

$$-\ln p = -\ln(t-s) = -\ln\left(1 - \frac{s}{t}\right) =$$

$$-\ln t - \ln\left(1 - \frac{s}{t}\right) = -\ln t + \frac{s}{t} + \frac{1}{2}\left(\frac{s}{t}\right)^2 + \frac{1}{3}\left(\frac{s}{t}\right)^3 + \frac{1}{4}\left(\frac{s}{t}\right)^4 + \ldots$$

In this case, the series development for the logarithm has been used in the final step. If this series development is terminated after the first order, then even this surprisingly results in more accurate scattered radiation correction than that in the case of the method described in the introductory part, in which the series development is likewise terminated after the first order. The present method therefore results in better scattered radiation correction, in which case the correction can advantageously be carried out using values that have already been converted to logarithmic form.

In principle, the proposed method produces sensible results even in the case of estimated scattered radiation signals which are greater than individual measurement signals, and this means that the problems mentioned further above do not occur.

In one preferred refinement of the method according to the invention, before the correction of each measurement signal t, a value is calculated for s/t, and the correction value is then read from a look-up table, which has been calculated in advance and contains correction values as a function of s/t. This look-up table can therefore be used independently of the object through which radiation is currently being passed, since it contains only correction values as a function of different ratios of s/t. Furthermore, this involves less computation complexity during X-ray imaging, so that the recorded and corrected images can be displayed in real time.

In order to further improve the accuracy for the proposed scattered radiation correction, it is also possible to take account of higher-order terms, for example second, third or fourth-order terms, by not terminating the specified series development until after terms of this order.

The respective scattered radiation signal is in this case determined in advance in the same way as that already used until now in the prior art. This may be done on measurement using one or more phantoms or by computational estimation as a function of the thickness of the examination object. In this case as well, of course, it is possible to carry out different corrections for different detector elements in the X-ray detector being used, if the previously determined scattered radiation components differ for individual detector elements.

The X-ray imaging system proposed for carrying out the method has at least one X-ray source and one X-ray detector opposite the X-ray source, between which the examination area for the examination object to be located in extends. The X-ray imaging system has a signal processing device for processing the measurement signals which are supplied from the X-ray detector, to be precise from the individual detector elements in the X-ray detector. The signal processing device is designed such that it converts the measurement signals to logarithmic form and subtracts correction values, which have been obtained from the series development of the logarithm in (1−s/t), from the measurement signals that have been converted to logarithmic form, with the series development being terminated at the earliest after the first order. In this case, s represents a previously determined scattered radiation signal for the X-ray detector, or the individual X-ray detector element, when radiation is passed through the examination object. The digitized measurement signal supplied from the X-ray detector or X-ray detector elements is t. The signal processing device in this case preferably also has a memory with a look-up table which contains the correction values as a function of s/t, and is designed such that, before the correction of each measurement signal t, it calculates the value for s/t and then reads the associated correction value from the look-up table. The signal processing device or the correction table may, of course, in this case also be designed such that the series development of the logarithm is terminated only after a higher order, for example after the second, third or fourth order.

In an X-ray imaging system such as this, the measurement signals are generally digitized by means of appropriate analog/digital converters adjacent to the X-ray detector itself, or on the path between the X-ray detector and the signal processing device. However, it is possible for the digitizing process also to be carried only in the signal processing device.

The proposed X-ray imaging system is preferably a computer-tomography scanner or a C-arc system which operates in a similar manner, in which the measurement signals of each projection pass through the proposed scattered radiation correction process in a corresponding manner.

The proposed method and the associated X-ray imaging system will be explained briefly once again in the following text using one exemplary embodiment and in conjunction with the drawings, without any restriction to the scope of protection stipulated by the patent claims. In this case:

FIG. 1 shows a schematic illustration of one example of the method procedure for carrying out the method according to the invention;

FIG. 1 shows an example of the method procedure for carrying out the method according to the invention using a single measurement signal t which is supplied from a detector element in the X-ray detector in a computer-tomography scanner. The measurement signal t is in this case converted to logarithmic form after having been digitized in the signal processing device, resulting in the negative logarithm −lnt. The ratio of a scattered radiation signal s which has previously been determined or estimated for that examination object to the measurement signal t is then formed, and an associated correction value for this ratio is read from a look-up table. The correction value is then subtracted from the logarithm of the measurement signal, or is added to the negative logarithm, in order to obtain the negative logarithm of the primary signal p. This negative logarithm −lnp is a measure of the attenuation of the X-ray beam from the X-ray source to the corresponding detector element on a straight-line path through the examination object. The image data is then processed further on the basis of these corrected primary radiation signals which have been converted to negative logarithmic form, that is to say either by the direct image display of the image resulting from the radiation having been passed through the object, or by image reconstruction in the case of a computer-tomography scan.

Figure 2A:
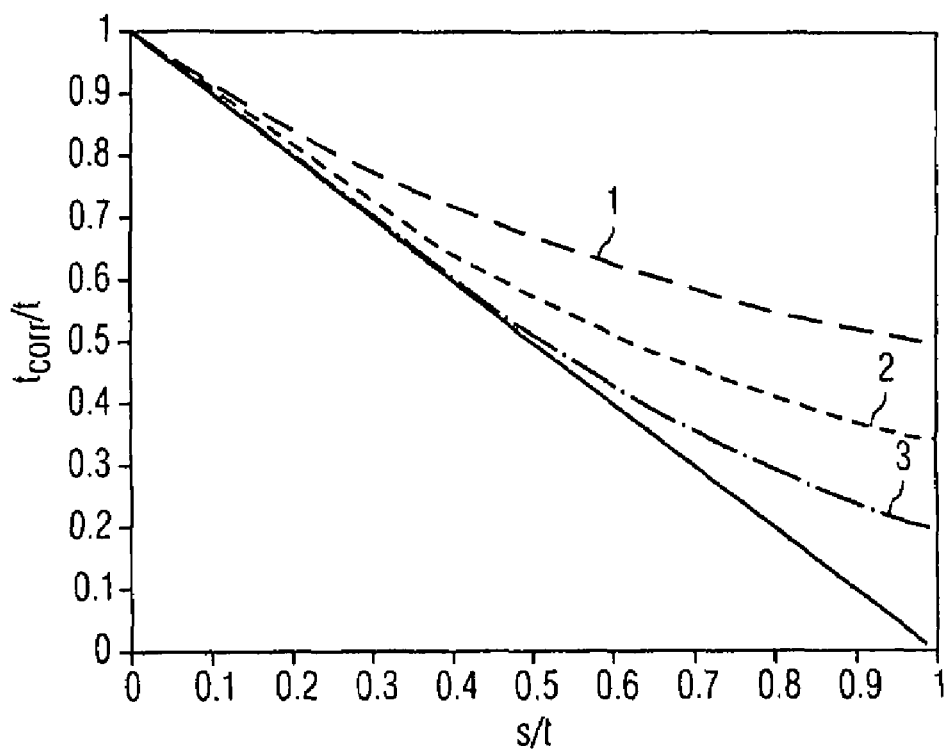
FIG. 2 shows a comparison between the accuracy of correction before logarithmic conversion and correction according to the proposed method after logarithmic conversions.
Figure 2B:
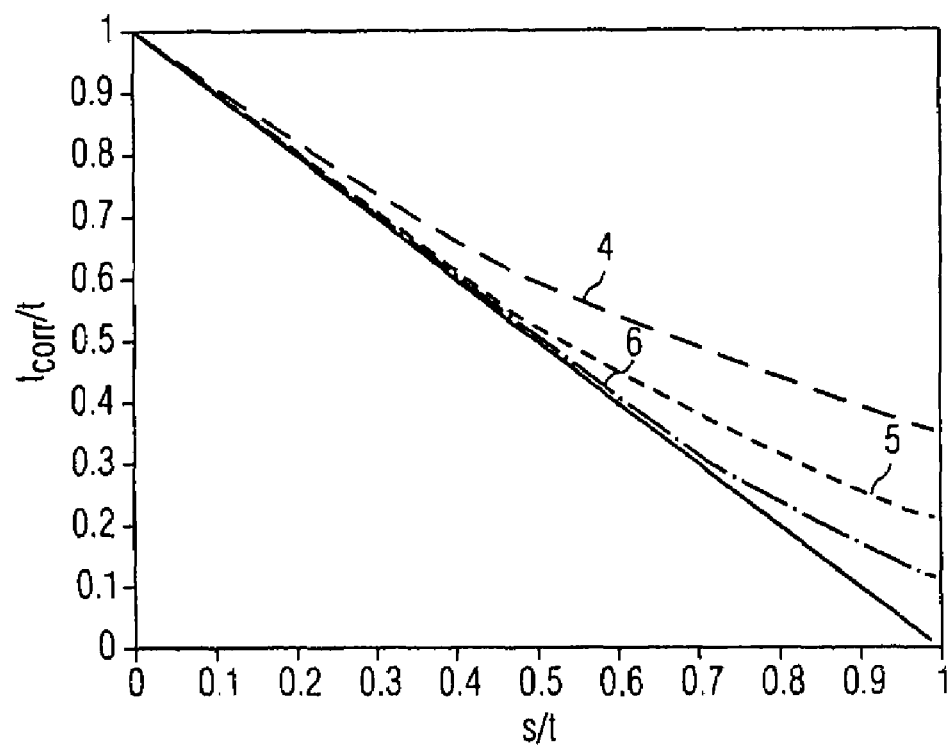

FIG. 2 shows a comparison of the accuracy of the correction using the present method (FIG. 2b) with the accuracy of the correction using the prior art (FIG. 2a), in which the correction is carried out before logarithmic conversion. For comparative purposes, each of the illustrations shows the ideal exact correction by means of the solid lines. The other lines in FIG. 2a show the result of correction by multiplication in the series development up to the first order (line 1) for series development up to the second order (line 2), and for series development up to the fourth order (line 3).

In the same way, the various lines in FIG. 2b show logarithmic correction using the proposed method with the series development being terminated after the first order (line 4), with the series development being terminated after the second order (line 5), and with the series development being terminated after the fourth order (line 6). Comparison of the two figures clearly shows that greater accuracy is achieved by logarithmic correction, of the same order.

Figure 3:
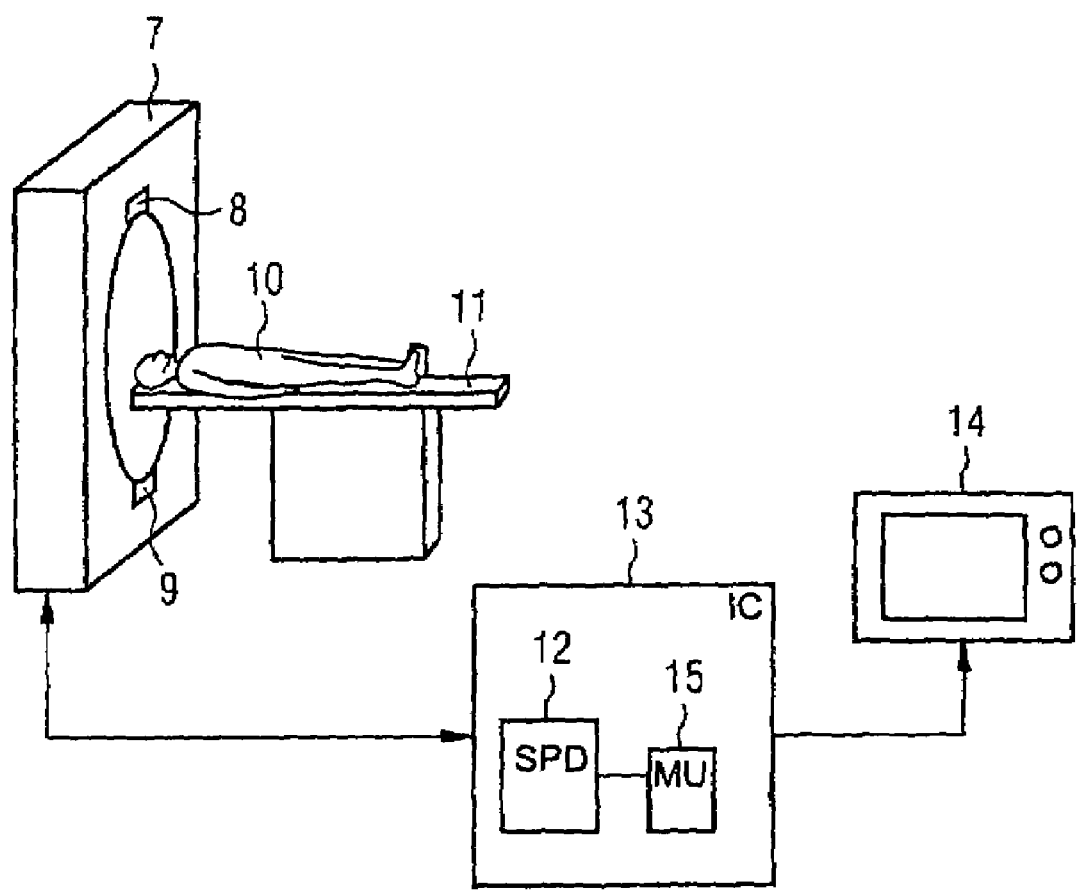
FIG. 3 shows a schematic illustration of one exemplary embodiment of the proposed X-ray imaging system.

Finally FIG. 3 shows a computer-tomography scan, in a highly schematic form and as one example of the proposed X-ray imaging system, in which an arrangement comprising an X-ray tube 8 and an opposite X-ray detector 9 rotates about an examination area in a rotating frame 7. The examination object, a patient 10, is in this case located in a known manner on patient couch 11, which can be moved through the examination area. The measurement signals obtained from the X-ray detector are digitized by an A/D converter, which is not illustrated but is adjacent to the X-ray detector, and are passed to a signal processing device 12, which is a component of an image computer 13 of the computer-tomography scanner. The scattered radiation correction on the basis of the proposed method is carried out by means of an appropriately designed software programme in the signal processing device 12. The corrected signals are then processed further in the image computer 13 for image reconstruction and image display on a monitor 14. By way of example, FIG. 3 also shows the memory unit 15 with the look-up table.

What is claimed is:

1. A method for scattered radiation correction in X-ray imaging, comprising:
   digitizing and converting measurement signals t from an X-ray detector to logarithmic form, the measurement signals t having been obtained by radiation through an examination object;
   subtracting correction values, which have been obtained from a series development of a logarithm $\ln(1-s/t)$, from the digitized and converted measurement signals, the series development being terminated at least after the first order, where s denotes a previously determined scattered radiation signal from radiation passed through the examination object.

2. The method as claimed in claim 1, further comprising:
   calculating a look-up value for s/t before the subtracting, and
   reading the correction values are from a look-up table before the subtracting, where the look-up table is calculated in advance and includes a plurality of correction values as a function of the calculated look-up value for s/t.

3. The method as claimed in claim 1, wherein the series development is terminated after a second order.

4. The method as claimed in claim 1, wherein the series development is terminated after a fourth order.

5. The method as claimed in claim 1, wherein the previously determined scattered radiation signal s does not have a same value for all detector elements of the X-ray detector.

6. An X-ray imaging system, comprising:
   at least one X-ray source;
   an X-ray detector opposite the at least one X-ray source; and
   a signal processing device to process measurement signals t produced by the X-ray detector when radiation is passed through an examination object, the signal processing device being designed to convert the measurement signals t to logarithmic form and subtract correction values from the converted measurement signals, the correction values being obtained from a series development of a logarithm $\ln(1-s/t)$, which is terminated at least after the first order, where s denotes a previously determined scattered radiation signal from radiation passed through the examination object.

7. The X-ray imaging system as claimed in claim 6, wherein the signal processing device includes a memory with a look-up table, where a look-up value is calculated for s/t before the correction values are subtracted from the converted measurement signals, and the correction values are read from a look-up table, the look-up table calculated in advance and including the correction values as a function of the calculated look-up value s/t.

8. The method as claimed in claim 2, wherein the series development is terminated after a second order.

9. The method as claimed in claim 2, wherein the series development is terminated after a fourth order.

10. The method as claimed in claim 2, wherein the previously determined scattered radiation signal s does not have a same value for all detector elements of the X-ray detector.

11. The method as claimed in claim 3, wherein the previously determined scattered radiation signal s does not have a same value for all detector elements of the X-ray detector.

12. The method as claimed in claim 4, wherein the previously determined scattered radiation signal s does not have a same value for all detector elements of the X-ray detector.

13. The method as claimed in claim 8, wherein the previously determined scattered radiation signal s does not have a same value for all detector elements of the X-ray detector.

14. The method as claimed in claim 9, wherein the previously determined scattered radiation signal s does not have a same value for all detector elements of the X-ray detector.

15. A computer readable medium including program segments for, when executed on a computer device, causing the computer device to implement the method of claim 1.

* * * * *